United States Patent
Deguchi et al.

(10) Patent No.: US 11,524,929 B2
(45) Date of Patent: *Dec. 13, 2022

(54) METHOD FOR PRODUCING ALPHA-ALLYLATED CYCLOALKANONE

(71) Applicant: Kao Corporation, Tokyo (JP)

(72) Inventors: Jun Deguchi, Tokyo (JP); Makoto Sakakibara, Wakayama (JP); Daichi Sakoda, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/440,284

(22) PCT Filed: Mar. 17, 2020

(86) PCT No.: PCT/JP2020/011627
§ 371 (c)(1),
(2) Date: Sep. 17, 2021

(87) PCT Pub. No.: WO2020/189661
PCT Pub. Date: Sep. 24, 2020

(65) Prior Publication Data
US 2022/0153671 A1   May 19, 2022

(30) Foreign Application Priority Data
Mar. 18, 2019   (JP) .............................. JP2019-049618

(51) Int. Cl.
*C07C 45/45* (2006.01)
*C07C 45/61* (2006.01)

(52) U.S. Cl.
CPC .............. *C07C 45/45* (2013.01); *C07C 45/61* (2013.01)

(58) Field of Classification Search
CPC ............................... C07C 45/45; C07C 45/61
See application file for complete search history.

(56) References Cited

U.S. PATENT DOCUMENTS

| 4,335,262 A | 6/1982 | Schulte-Elte et al. |
| 2012/0088935 A1 | 4/2012 | Schelper et al. |
| 2016/0031783 A1 | 2/2016 | Micoine et al. |

FOREIGN PATENT DOCUMENTS

| FR | 2 645 530 A1 | 10/1990 |
| JP | 63-2946 A | 1/1988 |
| JP | 2002-105010 A | 4/2002 |
| JP | 2014-500237 A | 1/2014 |
| JP | 2015-533799 A | 11/2015 |
| JP | 2016-34937 A | 3/2016 |
| WO | WO 2012/045786 A1 | 4/2012 |
| WO | WO 2015/036402 A1 | 3/2015 |
| WO | WO 2018/011386 A1 | 1/2018 |

OTHER PUBLICATIONS

International Search Report dated Jun. 9, 2020 in PCT/JP2020/011627 filed on Mar. 17, 2020, 3 pages.
Howard, W. L. et al., "Cyclohexanone Diallyl Acetal," Organic Syntheses, Coll., vol. 5, 1973, p. 292, 4 total pages.
Gardi, R. et al., "Alchilazione di steroidi mediante trasposizione secondo Claisen di eteri allilici.—Nota II. Trasposizione di enoleteri di 17-chetosteroidi.," Gazzetta Chimica Italiana, vol. 95, No. 4, 1965, pp. 351-367 (with English abstract).
"4.1 Synthesis from carbonyl compounds and alcohols," The Chemical Society of Japan, 4th Edition Experimental Chemistry Course 20, Organic Synthesis II, 1992, 20 total pages (with unedited computer-generated English translation).
Dubs, P. et al., "Novel Synthesis of a [10] (2,6)Pyridinophane, a Structural Isomer of Muscopyridine" J.C.S. Chem. Comm., 1976, p. 1021.
Wohl, R. A., "A Convenient One-Step Procedure for the Synthesis of Cyclic Enol Ethers. The Preparation of 1-Methoxy-1-cycloalkenes.," Synthesis, 1974, pp. 38-40.
Rautenstrauch, V. et al., "92. A Short Synthesis of (±)-Muscone," Helvetica Chimica Acta, vol. 73, 1990, pp. 896-901.
Sugiura, M. et al., "Regiochemical Control in the Pd(II)-Catalyzed Claisen Rearrangement via In Situ Enol Ether Exchange," Tetrahedron Letters, vol. 37, No. 44, 1996, pp. 7991-7994.
Howard, W. L. et al., "2-ALLYLCYCLOHEXANONE," Organic Synthesis, Coll., vol. 5, 1973, p. 25, 3 total pages.
A. Kasai, et al., "On Steroids. CXXVII. Preparation of Some Cyclic Steroidal Ethers" Collection Czechoslov. Chem. Commun., vol. 34, 1969, pp. 3479-3496.
Ohloff, G., Becker, J. and Schulte-Eite, K.H. (1967), Synthese von Exalton und racemischem Muscon aus Cydododecanon Vorlaeufige Mitteilung. HCA, 50: 705-708.

(Continued)

*Primary Examiner* — Sikarl A Witherspoon
(74) *Attorney, Agent, or Firm* — Oblon, McClelland, Maier & Neustadt, L.L.P.

(57) ABSTRACT

Provided is a method with which an α-allylated cycloalkanone is obtained from a cyclic compound cycloalkanone used as a starting material. The method is a method for producing an α-allylated cycloalkanone represented by General Formula (III), and the method includes: a step 1: reacting a compound represented by General Formula (I) and alcohol having 1 or more and 4 or less of carbon atoms in the presence of a first acid catalyst and optionally a dehydrating agent; and a step 2: reacting a crude product obtained in the step 1 and a compound represented by General Formula (II) in the presence of a second acid catalyst to produce an α-allylated cycloalkanone represented by General Formula (III). The step 1 and the step 2 are consecutively performed. In the formulae above, the group $-A^1-$ (it should be noted that the front bond refers to a bond that binds to the carbon atom $C^1$ and the back bond refers to a bond that binds to the carbon atom $C^2$) is an alkylene group having 4 or more and 20 or less of carbon atoms that optionally contains a hetero atom and optionally has a substituent, and $R^4$ is a hydrogen atom or an alkyl group having 1 or more and 4 or less of carbon atoms.

15 Claims, No Drawings

(56) References Cited

OTHER PUBLICATIONS

Knopff, O., and J Kuhne. "New Practical Synthesis of the Exceptional Musk Odorants (R)- Muscone and (R,Z)-5-Muscenone". CHIMIA, vol. 62, No. 6, Jun. 2008, p. 489,doi:10.253/chimia.2006. 480.
Fehr, C., Galindo, J. and Etter, O. (2004),:€, an Efficient Enentbsetective Synthesis of (+)-(R,Z)-5-Muscenone and (—)-(R)-Muscone- An Example of a Kinetic Resolution and Enantioconvergent Transformation. Eur. J. Org. Chem., 2004: 1953-1957.
Office Action dated Aug. 4, 2022, in corresponding Israeli Patent Application No. 286356.

METHOD FOR PRODUCING ALPHA-ALLYLATED CYCLOALKANONE

TECHNICAL FIELD

The present invention relates to a method for producing an α-allylated cycloalkanone represented by General Formula (III).

BACKGROUND ART

Macrocyclic compounds are known to exhibit activity useful in the fields of pharmaceutical drugs, perfume, agricultural chemicals, and the like. Muscenone, which is one type of macrocyclic ketone, is a highly biodegradable perfume material with high scent persistence and elegant feel. In order to meet increasing needs of easily degradable synthetic musk materials in recent years, there is demand for the development of a safe and highly efficient production method.

[Chemical Formula 1]

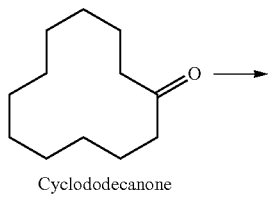

Cyclododecanone

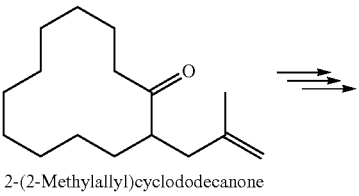

2-(2-Methylallyl)cyclododecanone

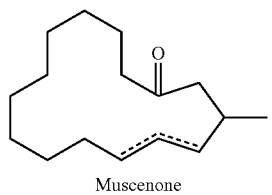

Muscenone

Muscenone can be obtained using a method including a step of allylating the α-site of cyclododecanone to obtain 2-(2-methylallyl)cyclododecanone and several steps of converting 2-(2-methylallyl)cyclododecanone. The following method is reported as the method for allylating the α-site of cyclododecanone. Cyclododecane is reacted with methanol in the presence of p-toluenesulfonic acid, and then 1,1-dimethoxycyclododecanone is isolated using a packed column. A method is also reported in which the obtained 1,1-dimethoxycyclododecanone is reacted with crotyl alcohol in the presence of propionic acid to produce 2-(1-methylaryl)cyclododecanone (Patent Document 1).

[Chemical Formula 2]

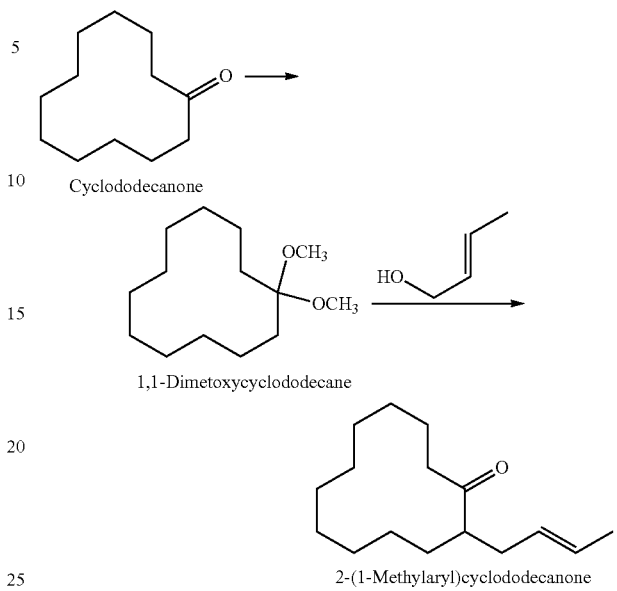

Moreover, a reaction for introducing an allyl group to the α-site of a cyclic ketone that is not a macrocyclic compound is reported (Non-Patent Document 1). Cyclohexanone is reacted with allyl alcohol in the presence of p-toluenesulfonic acid monohydrate, and then cyclohexanone diallylaceal is isolated through distillation under reduced pressure. Next, cyclohexanone diallylacetal is heated in the presence of p-toluenesulfonic acid to produce 2-allylcyclohexanone (Non-Patent Document 1). With this method, the yield is approximately 85 to 91%.

[Chemical Formula 3]

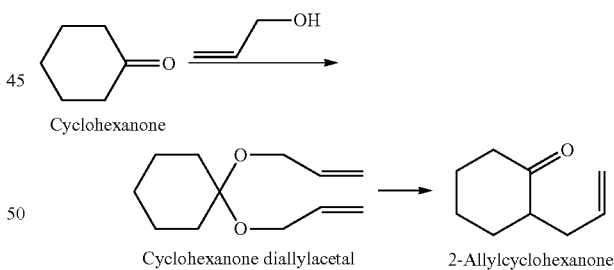

CITATION LIST

Patent Document

Patent Document 1: JP 2015-533799A

Non-Patent Document

Non-Patent Document 1: W. L. Howard, N. B. Lorette, Organic Synthesis, Vol. 5, 1973, p. 292

DISCLOSURE OF INVENTION

Problem to be Solved by the Invention

It is known that cycloalkanones as starting materials are reacted in the presence of various acids in order to produce α-allylated cycloalkanones as mentioned above. However, a method has not been known with which a highly pure α-allylated cycloalkanone is obtained in increased yield.

It is an object of the present invention to provide a method with which a highly pure α-allylated cycloalkanone is obtained in increased yield from a cyclic compound cycloalkanone used as a starting material.

Means for Solving Problem

Surprisingly, the inventors of the present invention found that, when a cycloalkanone was reacted with alcohol in the presence of an acid catalyst, and then was reacted with vinyl alcohol in the presence of an acid catalyst without performing an isolation-purification step, a highly pure α-allylated cycloalkanone was obtained in increased yield.

That is, the present invention is directed to a method for producing an α-allylated cycloalkanone represented by General Formula (III) (also referred to as a "compound of Formula (III)" or a "compound (III)" hereinafter), and the method includes:

a step 1: reacting a compound represented by General Formula (I) (cycloalkanone) (also referred to as a "compound of Formula (I)" or a "compound (I)" hereinafter) and alcohol having 1 or more and 4 or less of carbon atoms in the presence of a first acid catalyst and optionally a dehydrating agent; and a step 2: reacting a crude product obtained in the step 1 and a compound represented by General Formula (II) (also referred to as a "compound of Formula (II)" or a "compound (II)" hereinafter) in the presence of a second acid catalyst to produce an α-allylated cycloalkanone represented by General Formula (III), wherein the step 1 and the step 2 are consecutively performed.

[Chemical Formula 4]

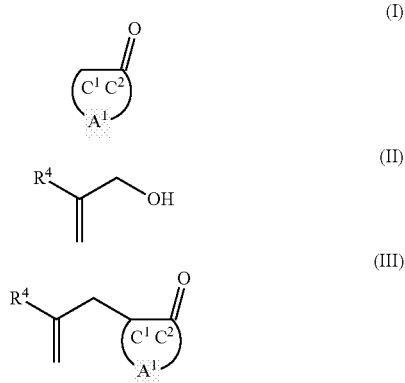

In the formulae above, the group -A$^1$- (it should be noted that the front bond refers to a bond that binds to the carbon atom C$^1$ and the back bond refers to a bond that binds to the carbon atom C$^2$) is an alkylene group having 4 or more and 20 or less of carbon atoms that optionally contains a hetero atom and optionally has a substituent, and R$^4$ is a hydrogen atom or an alkyl group having 1 or more and 4 or less of carbon atoms.

Effects of the Invention

With the present invention, it is possible to obtain an α-allylated cycloalkanone in increased yield and a highly pure product in increased yield from a cyclic compound cycloalkanone used as a starting material.

DISCLOSURE OF INVENTION

In the specification of the present application, "muscenone" is perfume manufactured by Firmenich SA (Geneva, Switzerland), which is a racemic mixture of various isomers. Specifically, muscenone is mainly a generic name for a mixture of Z-3-methyl-cyclopentadec-5-en-1-one, E-3-methyl-cyclopentadec-5-en-1-one, E-3-methyl-cyclopentadec-4-en-1-one, and Z-3-methyl-cyclopentadec-4-en-1-one.

Compound of Formula (I), Compound of Formula (II), Compound of Formula (III), Compound of Formula (XX), and Compound of Formula (XXI)

In the compound of Formula (I) above, the compound of Formula (III) above, a compound of Formula (XX), and a compound of Formula (XXI), the "alkylene group having 4 or more and 20 or less of carbon atoms" in the "alkylene group having 4 or more and 20 or less of carbon atoms that optionally contains a hetero atom and optionally has a substituent" that corresponds to the group -A$^1$- is represented as a group —(CH$_2$)$_4$—, a group —(CH$_2$)—, a group —(CH$_2$)$_6$—, a group —(CH$_2$)$_7$—, a group —(CH$_2$)$_8$—, a group —(CH$_2$)$_9$—, a group —(CH$_2$)$_{10}$—, a group —(CH$_2$)$_{11}$—, a group —(CH$_2$)$_{12}$—, a group —(CH$_2$)$_{13}$—, a group —(CH$_2$)$_{14}$—, a group —(CH$_2$)$_5$—, a group —(CH$_2$)$_{16}$—, a group —(CH$_2$)$_{17}$—, a group —(CH$_2$)$_{18}$—, a group —(CH$_2$)$_{19}$—, or a group —(CH$_2$)$_{20}$—. From the viewpoint that the obtained compound of General Formula (III) is used as a precursor of a perfume compound and/or that the temperature rises during the synthesis of the compound of Formula (III) (during the step 1 and the step 2), the "alkylene group having 4 or more and 20 or less of carbon atoms" is preferably alkylene having 6 or more and 14 or less of carbon atoms, more preferably alkylene having 8 or more and 14 or less of carbon atoms, even more preferably alkylene having 10 or more and 14 or less of carbon atoms, and even more preferably alkylene having 10 or more and 12 or less of carbon atoms.

In the compound of Formula (I), the compound of Formula (III), the compound of Formula (XX), and the compound of Formula (XXI), the "alkylene group having 4 or more and 20 or less of carbon atoms that optionally contains a hetero atom" in the "alkylene group having 4 or more and 20 or less of carbon atoms that optionally contains a hetero atom and optionally has a substituent" that corresponds to the group -A$^1$- may contain an oxygen atom, a nitrogen atom, and/or a sulfur atom as the hetero atom. That is, the "alkylene group having 4 or more and 20 or less of carbon atoms that optionally contains a hetero atom" is an alkylene group having 4 or more and 20 or less of carbon atoms that optionally contains one or more of an ether bond (—O—), an ester bond (—C(=O)—O— or —O—C(=O)—), and a thioether group (—S—), which do not inhibit the reaction. Examples of the above-mentioned "alkylene group having 4 or more and or less of carbon atoms that optionally further contains one or more of an ether bond, an ester bond, and a thioether group" include a group —(CH$_2$)$_2$—O—(CH$_2$)—, a group —(CH$_2$)$_2$—O—(CH$_2$)$_6$—, a group —(CH$_2$)$_3$—O—(CH$_2$)$_5$—, a group —(CH$_{24}$—O—(CH$_2$)$_4$—, a group —(CH$_2$)$_2$O—(CH$_2$)$_7$—, a group —(CH$_2$)$_3$—O—(CH$_2$)$_6$—, a group —(CH$_2$)$_4$—O—(CH$_2$)$_5$—, a group —(CH$_2$)—O—(CH$_2$)$_9$—, a group —(CH$_2$)$_2$—O—(CH$_2$)$_8$—, a group —(CH$_2$)$_3$—O—(CH$_2$)$_7$—, a group —(CH$_2$)$_4$—O—(CH)$_6$—, a group —(CH$_2$)$_5$—O—(CH$_2$)$_5$—, and a group —(CH$_2$)$_2$—NH—(CH$_2$)$_2$—, and, from the viewpoint that the obtained compound of General Formula (III) is used as a precursor of a perfume compound, the group —(CH$_2$)—O—(CH$_2$)$_9$—, the group —(CH$_2$)$_{20}$—(CH$_2$)$_8$—, the group —(CH$_2$)$_3$—O—(CH$_2$)$_7$—, the group —(CH$_2$)$_4$—O—(CH$_2$)$_6$—, and the group —(CH$_2$)O—(CH$_2$)$_5$— are preferable.

The "alkylene group having 4 or more and 20 or less of carbon atoms that optionally contains a hetero atom and optionally has a substituent" that corresponds to the group -A$^1$- is an "alkylene group having 4 or more and 20 or less of carbon atoms that optionally contains a hetero atom" and that optionally has one or more, preferably one or two, substituents. Examples of the substituent include alkyl groups, alkoxy groups, alkylamino groups, alkoxycarbonyl groups, alkanoyl groups, aryl groups, aralkyl groups, aryloxy groups, acyloxy groups, a carboxy group, halogen atoms, carbocycles, and heterocycles. Alkyl groups, alkoxycarbonyl groups, and alkoxy groups are preferable, and alkyl groups are more preferable. It should be noted that, when the substituent is an alkyl group, the carbon atoms contained in the alkyl group are not contained in 4 or more and 20 or less of carbon atoms in the "alkylene group having 4 or more and 20 or less of carbon atoms that optionally contains a hetero atom".

Two or more of the substituents may be combined together to form a carbocycle or heterocycle together with atoms to which the substituents are attached.

In the compound of Formula (II) and the compound of Formula (III), R$^4$ is a hydrogen atom or an alkyl group having 1 or more and 4 or less of carbon atoms. R$^4$ is preferably a hydrogen atom or an alkyl group having 1 or more and 3 or less of carbon atoms, more preferably a hydrogen atom, —CH$_3$, or —C$_2$H$_5$, and even more preferably —CH$_3$, from the viewpoint that R$^4$ contributes to the formation of a stable conformation during the Claisen rearrangement, resulting in an increase in the yield of the compound of General Formula (III).

The compounds represented by General Formula (I) above are represented by the following formulae, for example. From the viewpoint that the obtained compound of General Formula (III) is used as a precursor of a perfume compound, the compound represented by Formula (vi), the compound represented by Formula (vii), the compound represented by Formula (viii), and the compound represented by Formula (ix) are preferable, and the compound represented by Formula (vii) and the compound represented by Formula (viii) are more preferable. The compound represented by Formula (vii) is cyclododecanone. It should be noted that the compound represented by Formula (vii) is a compound of Formula (I-1), which will be described later.

[Chemical Formula 5]

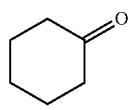

(i)

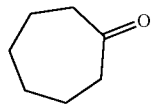

(ii)

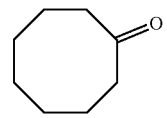

(iii)

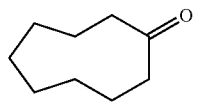

(iv)

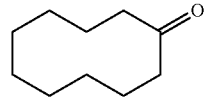

(v)

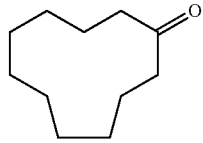

(vi)

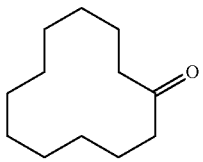

(vii)

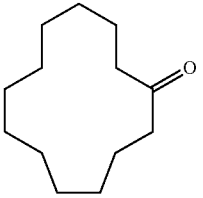

(viii)

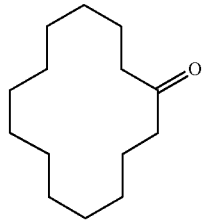

(ix)

The compounds represented by General Formula (I) above are commercially available or can be obtained using a known method such as the method disclosed in JP 2016-34937A.

The compounds represented by General Formula (II) above are represented by the following formulae, for example. From the viewpoint that the obtained compound of General Formula (III) is used as a precursor of a perfume compound, 6-methallyl alcohol, which is represented by Formula (62) below, is preferable. The compounds represented by General Formula (II) above are commercially available or can be obtained using a known method such as the method disclosed in JP 2002-105010A. It should be noted that the compound represented by Formula (62) is a compound of Formula (II-1), which will be described later.

[Chemical Formula 6]

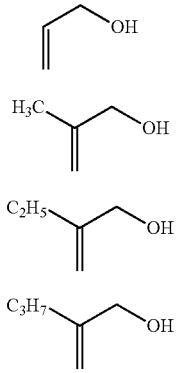

The compounds represented by General Formula (III) above are represented by the following formulae, for example. From the viewpoint that the obtained compound of General Formula (III) is used as a precursor of a perfume compound, the compound represented by Formula (xxvi), the compound represented by Formula (xxvii), the compound represented by Formula (xxviii), and the compound represented by Formula (xxix) are preferable, and the compound represented by Formula (xxvii) and the compound represented by Formula (xxviii) are more preferable. The compound represented by Formula (xxvii) is 2-(2-methylallyl)cyclododecanone. It should be noted that the compound represented by Formula (xxvii) is a compound of Formula (III-1), which will be described later.

[Chemical Formula 7]

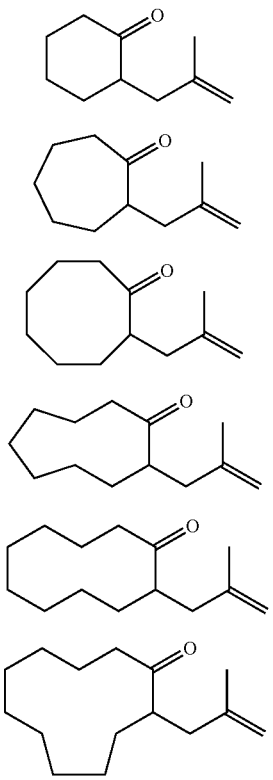

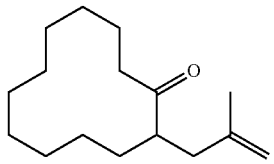

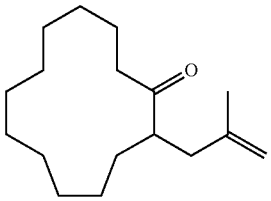

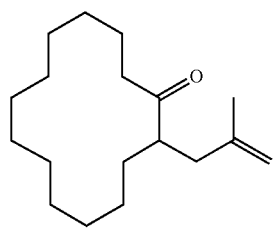

Method for Producing α-Allylated Cycloalkanone Represented by General Formula (III)

Step 1: Reacting Compound Represented by General Formula (I) and Alcohol Having 1 or more and 4 or less of Carbon Atoms in Presence of First Acid Catalyst and Optionally Dehydrating Agent Alcohol In the present invention, the above-mentioned alcohol is alcohol having 1 or more and 4 or less of carbon atoms. The alcohol is preferably saturated alcohol having 1 or more and 4 or less of carbon atoms. Examples of the alcohol include methanol, ethanol, 1-propanol, 1-butanol, and 2-methylpropanol.

First Acid Catalyst

In the present invention, the above-mentioned first acid catalyst may be one or more selected from the group consisting of organic sulfonic acids and salts thereof, and inorganic acid salts of pyridine. The organic sulfonic acids are for example, aromatic sulfonic acids or aliphatic sulfonic acids, and preferably aromatic sulfonic acids. The salts of organic sulfonic acids may be pyridinium salts.

Examples of the aromatic sulfonic acids and salts thereof include benzene-based aromatic compounds and salts thereof, and heteroaromatic compounds and salts thereof. The benzene-based aromatic compounds and salts thereof may be compounds having one benzene ring and salts thereof. Specific examples of the compounds having one benzene ring include benzenesulfonic acid, p-toluenesulfonic acid, 4-aminobenzenesulfonic acid, 2-aminobenzenesulfonic acid, 1H-benzimidazole-2-sulfonic acid, fluorobenzenesulfonic acid, difluorobenzenesulfonic acid, trifluorobenzenesulfonic acid, chlorobenzenesulfonic acid, dichlorobenzenesulfonic acid, and trichlorobenzenesulfonic acid. Among the compounds having one benzene ring, benzenesulfonic acid, p-toluenesulfonic acid, fluorobenzenesulfonic acid, difluorobenzenesulfonic acid, trifluorobenzenesulfonic acid, chlorobenzenesulfonic acid, dichlorobenzenesulfonic acid, and trichlorobenzenesulfonic acid are preferable, and p-toluenesulfonic acid is more preferable.

A specific example of salts of the compounds having one benzene ring is 2,4,6-trimethylpyridinium p-toluenesulfonate.

The benzene-based aromatic compounds and salts thereof may be compounds having two or more benzene rings and salts thereof, and specific examples thereof include naphthalenesulfonic acid and anthracenesulfonic acid.

The heteroaromatic compounds and salts thereof may be compounds containing a nitrogen atom. Specific examples of the heteroaromatic compounds and salts thereof include 5-isoquinolinesulfonic acid, 8-quinolinesulfonic acid, 6-quinolinesulfonic acid, 4-pyridineethanesulfonic acid, 2-pyridineethanesulfonic acid, and 3-pyridinesulfonic acid.

Excluding the benzene-based aromatic compounds and salts thereof and the heteroaromatic compounds and salts thereof, specific examples of the aliphatic sulfonic acids and salts thereof include methanesulfonic acid, trifluoromethanesulfonic acid, 10 camphorsulfonic acid, 4-monofolinpropanesulfonic acid, and salts thereof. Among the aliphatic sulfonic acids and salts thereof, trifluoromethanesulfonic acid and 10-camphorsulfonic acid are preferable, and 10-camphorsulfonic acid is more preferable.

Specific examples of acids included in the above-mentioned inorganic acid salts of pyridine include hydrochloric acid, sulfuric acid, nitric acid, phosphoric acid, sulfurous acid, nitrous acid, hydrobromic acid, and hydroiodic acid. In particular, among of these, hydrochloric acid, sulfuric acid, nitric acid, and phosphoric acid are preferable, and hydrochloric acid is more preferable.

In the present invention, the first acid catalyst may be selected from the group consisting of compounds represented by Formula (X) below and compounds represented by Formula (XI) below.

[Chemical Formula 8]

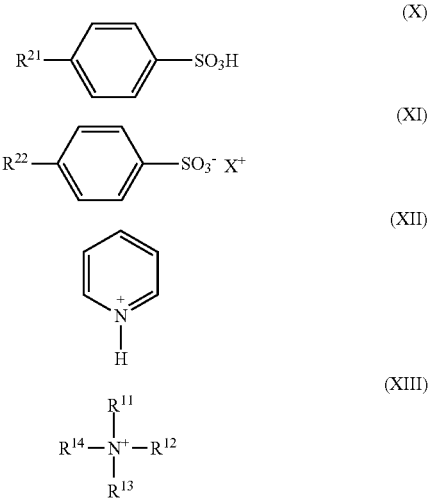

In the formulae above, $R^{21}$ and $R^{22}$ are independently a hydrogen atom or an alkyl group having 1 or more and 5 or less of carbon atoms, and $X^+$ is represented by Formula (XII) or Formula (XIII), where $R^{11}$, $R^{12}$, $R^{13}$, and $R^{14}$ are the same or different and each of them is a hydrogen atom or an alkyl group having 1 or more and 5 or less of carbon atoms.

In Formula (XIII) above, $R^{11}$, $R^{12}$, $R^{13}$, and $R^{14}$ each are preferably a hydrogen atom or an alkyl group having 1 or more and 3 or less of carbon atoms, more preferably a hydrogen atom, —$CH_3$, or —$C_2H_5$, and even more preferably —$CH_3$, from the viewpoint of producing the compound of General Formula (III) to be obtained in good yield.

In Formula (X) above, $R^{21}$ is preferably a hydrogen atom or an alkyl group having 1 or more and 3 or less of carbon atoms, more preferably a hydrogen atom, —$CH_3$, or —$C_2H_5$, and even more preferably —$CH_3$, from the viewpoint that volatilization of the compounds represented by Formula (X) is prevented even at high temperatures, isomerization of the compound of General Formula (I) is stably prevented, and the Claisen rearrangement is promoted.

In Formula (XI) above, $R^{22}$ is preferably a hydrogen atom or an alkyl group having 1 or more and 3 or less of carbon atoms, more preferably a hydrogen atom, —$CH_3$, or —$C_2H_5$, and even more preferably —$CH_3$, from the viewpoint that the compounds represented by Formula (XI) is a relatively weak acid, volatilization of the compounds represented by Formula (XI) is prevented even at high temperatures, isomerization of the compound of General Formula (II) is stably prevented, and the Claisen rearrangement is promoted.

From the viewpoint that ketalization of the compound of Formula (I) is promoted, examples of the first acid catalyst include p-toluenesulfonic acid and pyridinium p-toluenesulfonate, and p-toluenesulfonic acid and pyridinium p-toluenesulfonate are preferable.

In the present invention, the amount of the first acid catalyst that is used is preferably 10-5 equivalents or more, more preferably 10-4 equivalents or more, and even more preferably $5 \times 10^{-4}$ equivalents or more, and is preferably 1 equivalent or less, more preferably 0.5 equivalents or less, and even more preferably 0.2 equivalents or less, relative to the compound of Formula (I). The reason for this is that, when the amount of the first acid catalyst that is used is within the above-mentioned range, the first acid catalyst promotes the ketalization of the compound of Formula (I).

Dehydrating Agent Examples of the dehydrating agent include orthocarboxylic esters and sulfates. Specific examples of the dehydrating agent include trimethyl orthoformate, triethyl orthoformate, $Na_2SO_4$, and $MgSO_4$. The dehydrating agent is preferably an orthocarboxylic ester, more preferably trimethyl orthocarboxylate or trimethyl orthocarboxylate, and even more preferably trimethyl orthoformate. Using the dehydrating agent is preferable because the reaction in the step 1 is promoted. Accordingly, it is preferable to perform the step 1 in the presence of the first acid catalyst and the dehydrating agent.

Reaction Temperature

In the present invention, the step of reacting the compound of Formula (I) and alcohol having 1 or more and 4 or less of carbon atoms in the presence of the first acid catalyst and optionally the dehydrating agent is performed at a temperature of 120° C. or higher, for example, preferably 125° C. or higher, or more preferably 135° C. or higher, and 150° C. or lower, for example, or preferably 145° C. or lower. The reason for this is that, when this step is performed at a temperature within this range, the ketalization of the compound of Formula (I) is promoted.

Reaction Time

In the present invention, the reaction time of the step of reacting the compound of Formula (I) and alcohol having 1 or more and 4 or less of carbon atoms in the presence of the first acid catalyst and optionally the dehydrating agent is 2 hours to 5 days, for example, preferably 4 hours to 2 days, and more preferably 6 hours to 24 hours from the viewpoint of the production cost and production efficiency.

Reactor

In the present invention, it is preferable to perform the step 1 and the step 2, which will be described later, using a rectification column.

In the present invention, it is preferable to perform the step 1 and the step 2, which will be described later, in one pot. The term "in one pot" as used in the present invention means that two or more reactions are performed in the same container without distilling off an intermediate compound to the outside of the reaction system.

It should be noted that, in the present invention, the step 1 and the step 2 are consecutively performed and an isolation step is not involved, and thus a compound of Formula (XX) below and/or a compound of Formula (XXI) below are obtained through the step 1. $R^1OHR^2OH$ and/or $R^3OH$ correspond to the alcohol having 1 or more and 4 or less of carbon atoms in the step 1.

[Chemical Formula 9]

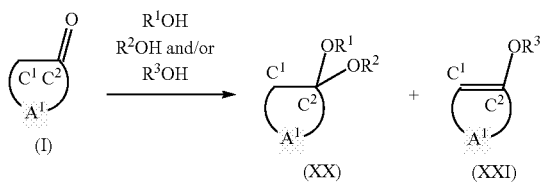

In the formulae above, $R^1$, $R^2$, and $R^3$ are the same or different and each of them is an alkyl group having 1 or more and 4 or less of carbon atoms, and the group -$A^1$- (it should be noted that the front bond refers to a bond that binds to the carbon atom $C^1$ and the back bond refers to a bond that binds to the carbon atom $C^2$) is an alkylene group having 4 or more and 20 or less of carbon atoms that optionally contains a hetero atom and optionally has a substituent.

Step 2: Reacting Crude Product Obtained in Step 1 and Compound Represented by General Formula (II) in Presence of Second Acid Catalyst to Produce α-Allylated Cycloalkanone Represented by General Formula (III)

Second Acid Catalyst

In the present invention, the above-mentioned second acid catalyst may be one or more selected from the group consisting of organic sulfonic acids and salts thereof, and inorganic acid salts of pyridine. The organic sulfonic acids are aromatic sulfonic acids or aliphatic sulfonic acids, and preferably aromatic sulfonic acids. The salts of organic sulfonic acids may be pyridinium salts.

Examples of the aromatic sulfonic acids and salts thereof include benzene-based aromatic compounds and salts thereof, and heteroaromatic compounds and salts thereof. The benzene-based aromatic compounds and salts thereof may be compounds having one benzene ring and salts thereof. Specific examples of the compounds having one benzene ring include benzenesulfonic acid, p-toluenesulfonic acid, 4-aminobenzenesulfonic acid, 2-aminobenzenesulfonic acid, 1H-benzimidazole-2-sulfonic acid, fluorobenzenesulfonic acid, difluorobenzenesulfonic acid, trifluorobenzenesulfonic acid, chlorobenzenesulfonic acid, dichlorobenzenesulfonic acid, and trichlorobenzenesulfonic acid. Among the compounds having one benzene ring, benzenesulfonic acid, p-toluenesulfonic acid, fluorobenzenesulfonic acid, difluorobenzenesulfonic acid, trifluorobenzenesulfonic acid, chlorobenzenesulfonic acid, dichlorobenzenesulfonic acid, and trichlorobenzenesulfonic acid are preferable, and p-toluenesulfonic acid is more preferable.

A specific example of salts of the compounds having one benzene ring is 2,4,6-trimethylpyridinium p-toluenesulfonate.

The benzene-based aromatic compounds and salts thereof may be compounds having two or more benzene rings and salts thereof, and specific examples thereof include naphthalenesulfonic acid and anthracenesulfonic acid.

The heteroaromatic compounds and salts thereof may be compounds containing a nitrogen atom. Specific examples of the heteroaromatic compounds and salts thereof include 5-isoquinolinesulfonic acid, 8-quinolinesulfonic acid, 6-quinolinesulfonic acid, 4-pyridineethanesulfonic acid, 2-pyridineethanesulfonic acid, and 3-pyridinesuofonic acid.

Excluding the benzene-based aromatic compounds and salts thereof and the heteroaromatic compounds and salts thereof, specific examples of the aliphatic sulfonic acids and salts thereof include methanesulfonic acid, trifluoromethanesulfonic acid, 10 camphorsulfonic acid, 4-monofolinpropanesulfonic acid, and salts thereof. Among the aliphatic sulfonic acids and salts thereof, trifluoromethanesulfonic acid and 10-camphorsulfonic acid are preferable, and 10-camphorsulfonic acid is more preferable.

Specific examples of acids included in the above-mentioned inorganic acid salts of pyridine include hydrochloric acid, sulfuric acid, nitric acid, phosphoric acid, sulfurous acid, nitrous acid, hydrobromic acid, and hydroiodic acid. In particular, out of these acids, hydrochloric acid, sulfuric acid, nitric acid, and phosphoric acid are preferable, and hydrochloric acid is more preferable.

In the present invention, the second acid catalyst may be selected from the group consisting of compounds represented by Formula (X) below and compounds represented by Formula (XI) below.

[Chemical Formula 10]

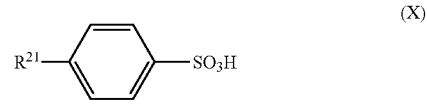

(X)

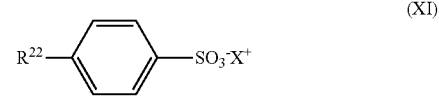

(XI)

(XII)

(XIII)

In the formulae above, $R^{21}$ and $R^{22}$ are independently a hydrogen atom or an alkyl group having 1 or more and 5 or less of carbon atoms, and $X^+$ is represented by Formula (XI) or Formula (XIII), where $R^{11}$, $R^{12}$, $R^{13}$, and $R^{14}$ are the same or different and each of them is a hydrogen atom or an alkyl group having 1 or more and 5 or less of carbon atoms.

In Formula (XIII) above, $R^{11}$, $R^{12}$, $R^{13}$, and $R^{14}$ each are preferably a hydrogen atom or an alkyl group having 1 or more and 3 or less of carbon atoms, more preferably a hydrogen atom, —$CH_3$, or —$C_2H_5$, and even more preferably —CH$_3$, from the viewpoint of producing the compound of General Formula (II) to be obtained in good yield.

In Formula (X) above, R$^{21}$ is preferably a hydrogen atom or an alkyl group having 1 or more and 3 or less of carbon atoms, more preferably a hydrogen atom, —CH$_3$, or —C$_2$H$_5$, and even more preferably —CH$_3$, from the viewpoint that volatilization is prevented even at high temperatures, isomerization of the compound of General Formula (II) is stably prevented, and the Claisen rearrangement is promoted.

In Formula (XI) above, R$^{22}$ is preferably a hydrogen atom or an alkyl group having 1 or more and 3 or less of carbon atoms, more preferably a hydrogen atom, —CH$_3$, or —C$_2$H$_5$, and even more preferably —CH$_3$, from the viewpoint that a relatively weak acid is obtained, volatilization is prevented even at high temperatures, isomerization of the compound of General Formula (HI) is stably prevented, and the Claisen rearrangement is promoted.

Examples of the second acid catalyst include p-toluenesulfonic acid and pyridinium p-toluenesulfonate, and p-toluenesulfonic acid and pyridinium p-toluenesulfonate are preferable.

In the present invention, the amount of the second acid catalyst that is used is preferably 10$^{-5}$ equivalents or more, more preferably 10$^{-4}$ equivalents or more, and even more preferably 5×10$^{-4}$ equivalents or more, and is preferably 1 equivalent or less, more preferably 0.5 equivalents or less, and even more preferably 0.2 equivalents or less, relative to the compound of Formula (I). The reason for this is that, when the amount of the second acid catalyst that is used is within the above-mentioned range, the second acid catalyst promotes the ketalization of the compound of Formula (I).

In the present invention, the second acid catalyst may be the same as or different from the first acid catalyst in the step 1. More preferably, in the present invention, the first acid catalyst in the step 1 and the second acid catalyst in the step 2 are the same. More preferably, in the present invention, the step 2 may be performed without substantially adding a catalyst after the step 1. In this case, the first acid catalyst is used as the second acid catalyst.

Consecutiveness

The present invention is directed to the method in which the step 1 and the step 2 are consecutively performed. The term "consecutively" as used in the present invention means that an operation need not be performed between the step 1 and the step 2, but the reaction system may be left to stand or be stored. When the step 1 and the step 2 are consecutively performed, an isolation-purification step need not be performed in the course of the method. It is preferable that the method in which the step 1 and the step 2 are consecutively performed includes no isolation-purification step performed in the course of the method. When the step 1 and the step 2 are consecutively performed, there is no need to remove a reaction by-product in perfume synthesis, and therefore, the method of the present invention is excellent.

Isolation-Purification Step

The term "isolation-purification step" as used in the present invention means an "operation to fractionate a compound to be used as a raw material in a subsequent step". Specifically, it means that "a compound to be used as a raw material in a subsequent step is fractionated by performing distillation to distill off the compound to the outside of the reaction system" or "a compound to be used as a raw material in a subsequent step is fractionated by silica gel column chromatography". In the present invention, the isolation-purification step does not include an operation to remove a solvent and a residual reagent in a reaction mixture through distillation and water-washing. For example, the isolation-purification step of the present application does not include a step in which distillation is performed at a pressure of 50 kPa or more but a compound to be used as a raw material in a subsequent step is not fractionated. For example, a step in which distillation is performed at a pressure of 5 kPa or less and a compound to be used as a raw material in a subsequent step is fractionated corresponds to the isolation-purification step of the present application.

Reaction Temperature

In the present invention, the step 2 is performed at a temperature of 120° C. or higher, for example, preferably 125° C. or higher, or more preferably 135° C. or higher, and 150° C. or lower, for example, or preferably 145° C. or lower. The reason for this is that, when this step is performed at a temperature within this range, alcohol (R$^1$OH, R$^2$OH, R$^3$OH) resulting from acetal exchange between a compound represented by General Formula (XX) and/or a compound represented by General Formula (XXI) and a compound represented by General Formula (II) can be volatilized to the outside of the reaction system, thus making it possible to accelerate the reaction.

Reaction Time

In the present invention, the reaction time of the step 2 is 2 hours to 5 days, for example, preferably 4 hours to 2 days, and more preferably 6 hours to 24 hours from the viewpoint of the production cost and production efficiency.

Furthermore, the present invention is directed to a method for producing an α-allylated cycloalkanone represented by General Formula (III), and the method includes:

a step 1: reacting a compound represented by General Formula (I) and alcohol having 1 or more and 4 or less of carbon atoms in the presence of a first acid catalyst and optionally a dehydrating agent; and a step 2: reacting a crude product obtained in the step 1 and a compound represented by General Formula (II) in the presence of a second acid catalyst to produce an α-allylated cycloalkanone represented by General Formula (III), wherein the first acid catalyst in the step 1 and the second acid catalyst in the step 2 are the same.

[Chemical Formula 11]

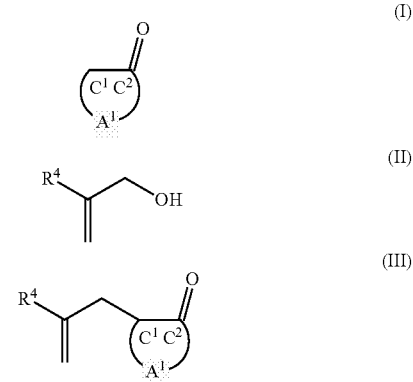

In the formulae above, the group -A$^1$- (it should be noted that the front bond refers to a bond that binds to the carbon atom C$^1$ and the back bond refers to a bond that binds to the carbon atom C$^2$) is an alkylene group having 4 or more and 20 or less of carbon atoms that optionally contains a hetero atom and optionally has a substituent, and $R^4$ is a hydrogen atom or an alkyl group having 1 or more and 4 or less of carbon atoms.

In the method of the present invention, it is preferable that Formula (I) above is Formula (I-1) below, and Formula (III) above is Formula (III-1) below. The reason for this is that the compound of Formula (III-1) useful in a method for synthesizing muscenone, which will be described later, can be obtained.

[Chemical Formula 12]

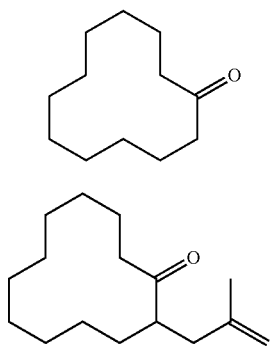

(I-1)

(III-1)

Furthermore, the present invention is directed to a method for synthesizing muscenone in which the α-allylated cycloalkanone of Formula (II-1) produced using the method mentioned above is used. Also, the present invention is directed to use of the α-allylated cycloalkanone of Formula (III-1) as a raw material of muscenone.

[Chemical Formula 13]

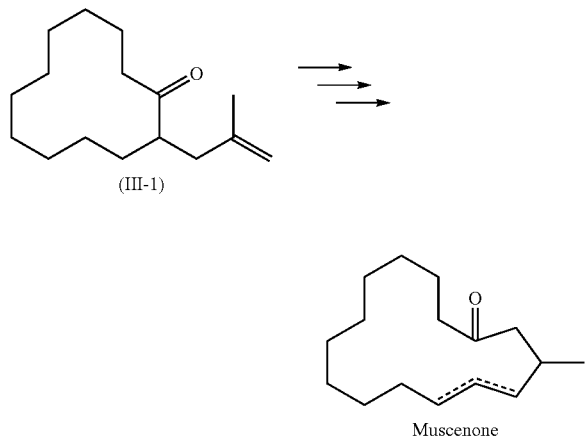

Specifically, the method for synthesizing muscenone includes the following steps:

(i) cyclization of the compound of Formula (III-1);
(ii) hydrogenation;
(iii) oxidative cleavage;
(iv) reduction; and
(v) ring-opening.

[Chemical Formula 14]

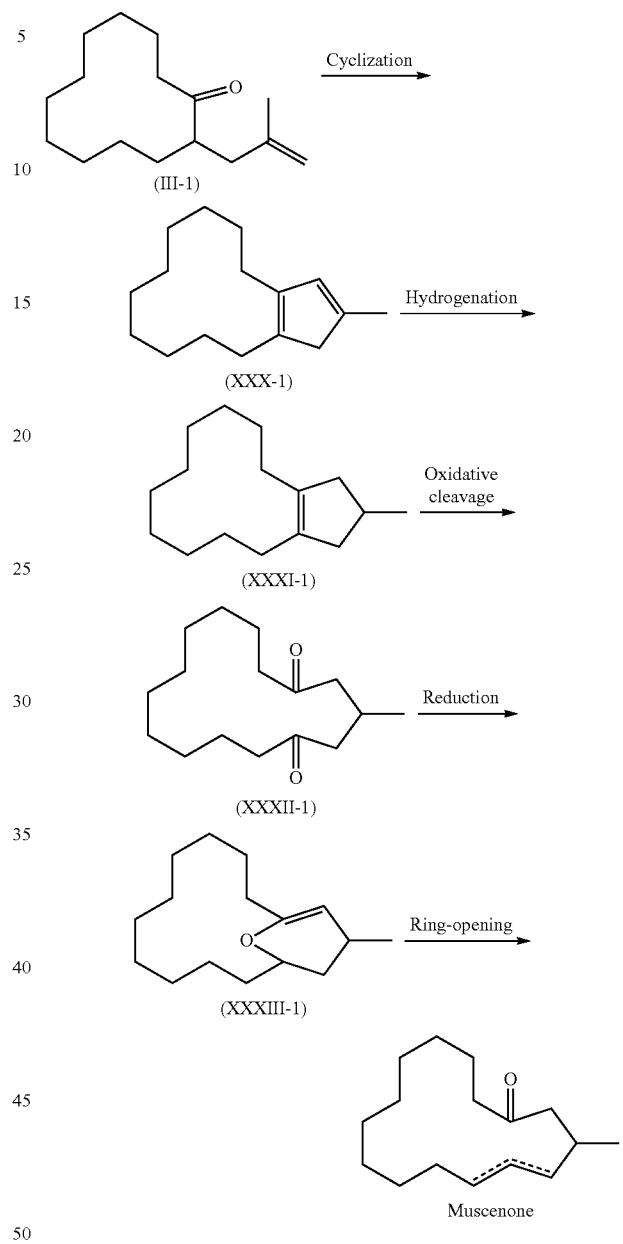

Regarding the above-described embodiments, the present invention further discloses the following methods.

<1> A method for producing an α-allylated cycloalkanone represented by General Formula (III), including:

a step 1: reacting a compound represented by General Formula (I) and alcohol having 1 or more and 4 or less of carbon atoms in the presence of a first acid catalyst and optionally a dehydrating agent; and a step 2: reacting a crude product obtained in the step 1 and a compound represented by General Formula (II) in the presence of a second acid catalyst to produce an α-allylated cycloalkanone represented by General Formula (III), wherein the step 1 and the step 2 are consecutively performed.

[Chemical Formula 15]

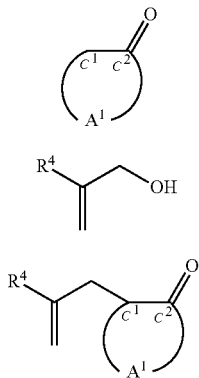

In the formulae above, the group $-A^1-$ (it should be noted that the front bond refers to a bond that binds to the carbon atom $C^1$ and the back bond refers to a bond that binds to the carbon atom $C^2$) is an alkylene group having 4 or more and 20 or less of carbon atoms that optionally contains a hetero atom and optionally has a substituent, and $R^4$ is a hydrogen atom or an alkyl group having 1 or more and 4 or less of carbon atoms.

<2> The method according to <1>, wherein the step 1 is performed in the presence of the first acid catalyst and the dehydrating agent.

<3> The method according to <1> or <2>, wherein the method in which the step 1 and the step 2 are consecutively performed includes no isolation-purification step performed in the course of the method.

<4> The method according to any one of <1> to <3>, wherein the first acid catalyst and the second acid catalyst are independently one or more selected from the group consisting of organic sulfonic acids and salts thereof, and inorganic acid salts of pyridine.

<5> The method according to <4>, wherein the organic sulfonic acids are aromatic sulfonic acids.

<6> The method according to <4> or <5>, wherein the first acid catalyst and the second acid catalyst are independently selected from the group consisting of compounds represented by Formula (X) below and compounds represented by Formula (XI) below.

[Chemical Formula 16]

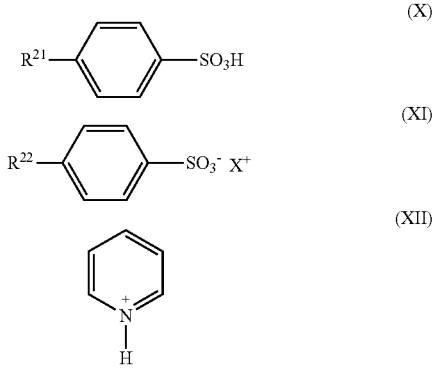

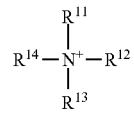

In the formulae above, $R^{21}$ and $R^{22}$ are independently a hydrogen atom or an alkyl group having 1 or more and 5 or less of carbon atoms, and $X^+$ is represented by Formula (XII) or Formula (XIII), where $R^{11}$, $R^{12}$, $R^{13}$, and $R^{14}$ are the same or different and each of them is a hydrogen atom or an alkyl group having 1 or more and 5 or less of carbon atoms.

<7> The method according to any one of <1> to <6>, wherein the first acid catalyst and the second acid catalyst independently contain p-toluenesulfonic acid or pyridinium p-toluenesulfonate.

<8> The method according to any one of <4> to <6>, wherein the salts of the organic sulfonic acids are pyridinium salts.

<9> The method according to <4>, wherein an acid included in the inorganic acid salts of pyridine is one or more selected from the group consisting of hydrochloric acid, sulfuric acid, nitric acid, phosphoric acid, sulfurous acid, nitrous acid, hydrobromic acid, hydroiodic acid, acetic acid, and butyric acid.

<10> The method according to any one of <1> to <9>, wherein the first acid catalyst and the second acid catalyst are the same.

<11> The method according to any one of <1> to <10>, wherein an amount of the first acid catalyst that is used is $10^{-5}$ equivalents or more and 1 equivalent or less relative to a total amount of the compound of General Formula (I) and the compound of General Formula (II).

<12> The method according to any one of <1> to <11>, wherein a reaction in the presence of the first acid catalyst is performed at a temperature of 120° C. or higher and 145° C. or lower.

<13> The method according to any one of <1> to <12>, wherein a reaction in the presence of the second acid catalyst is performed at a temperature of 120° C. or higher and 145° C. or lower.

<14> The method according to any one of <1> to <13>, wherein the first step and the second step are performed using a rectification column.

<15> The method according to any one of <1> to <14>, wherein the first step and the second step are performed in one pot.

<16> The method according to any one of <1> to <15>, wherein the Formula (I) is Formula (I-1) below, and the Formula (III) is Formula (III-1) below.

[Chemical Formula 17]

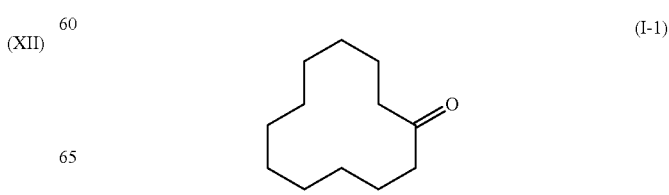

-continued

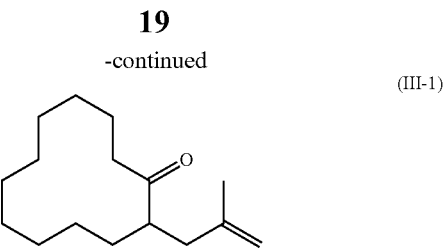
(III-1)

<17> A method for synthesizing muscenone in which an α-allylated cycloalkanone of Formula (III-1) produced using the method according to <16> is used.

EXAMPLES

Gas Chromatography (GC) Apparatus and Analysis Conditions
GC apparatus: Model: GC-6850, manufactured by Agilent Technologies
Column: DB-1 (with an inner diameter of 0.25 mm, a length of 30 m, and a membrane thickness of 0.25 μm), manufactured by J&W
Carrier gas: He, 1.5 mL/min
Injection conditions: 300° C., split ratio of 100/1
Injection amount: 1 μL
Detection conditions: FID method, 300° C.
Column temperature conditions: 80° C.→rising the temperature at 10° C./minute→keeping the temperature at 300° C. for 10 minutes
Compound Identification
Compounds obtained in examples, experimental examples, and the like below were identified using GC (gas chromatography).
The yield (%) was calculated using the following expression.

$$\text{Yield} = \frac{\begin{pmatrix} \text{Weight of reaction} \\ \text{end solution of} \\ 2\text{-}(2\text{-}methylallyl) \\ \text{cyclododecanone} \\ \text{GC area \%} \end{pmatrix} \times \frac{236.4}{182}}{\text{Feed amount of raw material (cyclododecanone)}} \times 100$$

[Mathematical Formula 1]

Here, a GC area % refers to a ratio of an output chart area of the component detected using GC to the entire area.

Example 1: Synthesis of 2-(2-methylallyl)cyclododecanone

[Chemical Formula 18]

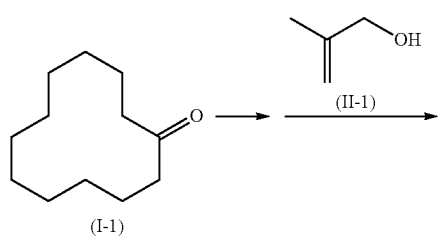

-continued

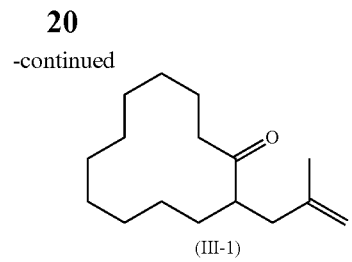
(III-1)

(i) Step 1
Cyclododecanone (I-1) (500.0 g, 2.743 mol), trimethyl orthoformate (349.5 g, 3.292 mol), and methanol (264.3 g, 8.229 mol) were placed into a 2-L four-neck flask and stirred at room temperature into a homogeneous solution. Pyridinium p-toluenesulfonate (PPTS, 0.7 g, 2.743 mmol) was added thereto, stirred, and dissolved. A thermometer, a mechanical stirrer, and a 10-step Sulzer rectification column (manufactured by Kyowa Chemical) were installed on the 2-L four-neck flask. Under a nitrogen atmosphere, stirring of the content in the 2-L four-neck flask was started at an outside temperature of 80° C. A reactant was sampled from the 2-L four-neck flask over time and subjected to GC analysis, and thus the conversion rate of the compound of (I-1) was observed. The reaction was stopped 6 hours after the start of the reaction, and the reaction mixture was cooled.

Next, methanol and trimethyl orthoformate contained in the product were distilled off under reduced pressure. A K-shaped pipe, a cooling pipe, and a distillate receiver were installed on the 2-L four-neck flask. Under a nitrogen atmosphere, distillation of the product under reduced pressure was started at an outside temperature of 110° C. The pressure was reduced from the ordinary pressure to 66.5 kPa one hour after the start of the distillation, and then the distillation under reduced pressure was continued. The flow of distillate into the receiver stopped in 2 hours, and the distillation under reduced pressure was finished. As a result of gas chromatography analysis on the reaction solution after the distillation, the component composition was as follows: 1,1-dimethoxycyclododecane (XX-1) corresponded to 43.5 GC area %, and 1-methoxy-1-cyclododecene (XXI-1) corresponded to 54.5 GC area %.

[Chemical Formula 19]

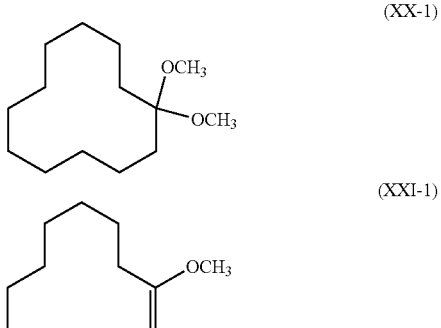

(ii) Step 2
A thermometer, a mechanical stirrer, and a 10-step Sulzer rectification column were installed on the 2-L four-neck flask containing the reactants. At room temperature, 6-methallyl alcohol (II-1) (296.7 g, 4.115 mol) was added to the four-neck flask. The content (containing pyridinium p-toluenesulfonate (PPTS, 0.7 g, 2.743 mmol)) in the flask was stirred into a homogeneous system, and then was heated in an oil bath at an outside temperature of 140° C. under nitrogen stream. The top temperature was monitored over time and was confirmed to be 65° C. After 3.5 hours, it was confirmed that the content in the flask became free of 1,1-dimetoxycyclododecane (XX-1) and 1-methoxy-1-cyclododecene (XXI-1), and then the reaction was stopped.

Next, a K-shaped pipe, a cooling pipe, and a distillate receiver were installed on the 2-L four-neck flask containing the reaction solution (containing 2-(2-methylallyl)cyclododecanone (III-1)), the reaction solution was heated and stirred at 18.0 kPa and 120° C. to distill off 6-methallyl alcohol (II-1) (distilled-off amount: 67.1 g). After the reaction solution was heated and stirred for 2 hours, the pressure was reduced to 16 kPa, and the reaction solution was heated and stirred for another 1 hour in order to complete the distillation.

After ß-methallyl alcohol (II-1) had been distilled off, the residue was transferred to a 2-L separable reaction container with a jacket, and then alkali water obtained by dissolving $K_2HPO_4$ (0.4 g, 2.057 mmol) in 20.2 g of ion-exchange water was added thereto. A mechanical stirrer, a thermometer, a Dimroth condenser, and a nitrogen-flow device were installed on the separable reaction container. The mixture in the separable reaction container was stirred at room temperature for 1 hour. After the stirring had been finished, the mixture was heated to 80° C. using a condenser and was then left to stand till layers were separated. An aqueous layer (15.4 g) was removed from the separable reaction container, and then the pH of the residue was checked. The pH was 8.0 (pH test paper).

Simple distillation was performed in order to distill off the residual ß-methallyl alcohol (II-1) and water from the residue. A K-shaped pipe, a cooling pipe, and a distillate receiver were installed on the separable reaction container containing the residue, the residue was heated and stirred at 0.3 kPa and 130° C. for 2 hours to distill off ß-methallyl alcohol (II-1) and water. Thus, a residue (671.2 g) was obtained. Gas chromatography analysis on the residue revealed that 2-(2-methylallyl)cyclododecanone (III-1) corresponded to 94.7 GC area %. The yield of 2-(2-methylallyl) cyclododecanone (III-1) calculated from the amount of 2-(2-methylallyl)cyclododecanone obtained was 98.1%.

Example 2: Synthesis of 2-(2-methylallyl)cyclododecanone

[Chemical Formula 20]

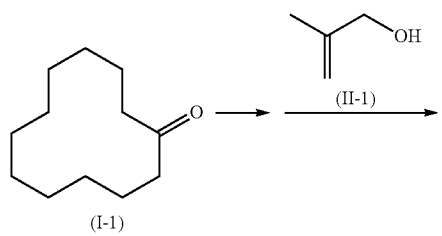

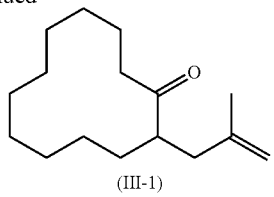

(i) Step 1

After cyclododecanone (I-1) (500.0 g, 2.743 mol), trimethyl orthoformate (349.3 g, 3.292 mol), and methanol (263.7 g, 8.229 mol) were placed into a 2-L four-neck flask, and the air was purged with nitrogen, the resultant mixture was stirred at room temperature for 4 hours under a nitrogen atmosphere into a homogeneous solution. Pyridinium p-toluenesulfonate (PPTS, 0.7 g, 2.743 mmol) was added thereto, stirred, and dissolved. A Dimroth condenser was attached to the 2-L four-neck flask, and a circulator was used to flow warm water at 37° C. in the Dimroth condenser. A Dean-Stark dewatering pipe was attached to an end of the Dimroth condenser, and a 200-mL distillate receiver was attached to the lower portion of the dewatering pipe. The distillate receiver was immersed in ice water and was thus cooled with ice. Another Dimroth condenser was attached to the upper portion of the Dean-Stark dewatering pipe, and another circulator was used to flow cold water at 10° C. in the Dimroth condenser. One end of a silicone tube was attached to the top of the Dimroth condenser cooled to 10° C., and the other end was introduced to an ethanol-dry ice trap. A portion beyond the trap was sealed with nitrogen. Under a nitrogen atmosphere, the content in the 2-L four-neck flask was heated and refluxed at a bath temperature of 80° C. for 8 hours.

A K-shaped pipe, a cooling pipe, and a distillate receiver were installed on the 2-L four-neck flask containing the reaction end product. Under a nitrogen atmosphere, the solvent was distilled off from the reaction end product at 101.3 kPa over 4.5 hours while the bath temperature was raised from 100° C. to 120° C. As a result of gas chromatography analysis on the reaction solution after the distillation, the component composition was as follows: 1,1-dimetoxycyclododecane (XX-1) corresponded to 25.9 GC area %, 1-methoxy-1-cyclododecene (XXI-1) corresponded to 73.7 GC area %, and cyclododecanone (I-1) corresponded to 0.3 GC area %.

(ii) Step 2

A K-shaped pipe, a cooling pipe, and a distillate receiver were installed on the 2-L four-neck flask containing the reactants. α-Methallyl alcohol (II-1) (296.7 g, 4.115 mol) was dripped into the four-neck flask over 8 minutes while the reactants were heated and stirred at a bath temperature of 110° C. under a nitrogen atmosphere. Methanol was distilled off at a bath temperature of 110° C. under nitrogen stream into the four-neck flask till the content of the methallyl cyclododecanone corresponded to 40 to 50 GC area %. After 4 hours, the flow of methanol from the four-neck flask stopped (distilled-off amount: 108.9 g). The K-shaped pipe, the cooling pipe, and the distillate receiver were removed from the four-neck flask, a Dimroth condenser was attached to the four-neck flask, the bath temperature was raised to 130° C., and then the reaction mixture was heated and refluxed for 17 hours.

Next, a K-shaped pipe, a cooling pipe, and a distillate receiver were installed on the 2-L four-neck flask containing the reaction solution, and the reaction solution was heated and stirred at 18.0 kPa and a bath temperature of 120° C. for 3.5 hours to distill off 8-methallyl alcohol (III-1) (distilled-off amount: 79.7 g). As a result of gas chromatography analysis on the reaction solution after the distillation, the component composition was as follows: 2-(2-methylallyl) cyclododecanone (III-1) corresponded to 92.5 area %.

Alkali water obtained by dissolving $K_2HPO_4$ (0.358 g, 2.057 mmol) in 20.0 g of ion-exchange water was added to the 2-L four-neck flask containing the reaction solution after 6-methallyl alcohol (II-1) had been distilled off under reduced pressure, and the resultant mixture was vigorously stirred at room temperature for 1 minute.

Next, the viscosity of the reaction solution was reduced by raising the bath temperature to 80° C., and then the reaction solution was left to stand for 15 minutes to separate layers. The pH of the aqueous layer of the reaction solution was 8.0 (pH test paper). As a result of gas chromatography analysis on the oil layer of the reaction solution, 2-(2-methylallyl) cyclododecanone (III-1) corresponded to 92.5 area %. The amount of the oil layer obtained was 644.9 g (theoretical amount: 648.5 g). The yield of 2-(2-methylallyl)cyclododecanone (III-1) calculated from the amount of 2(2-methylallyl)cyclododecanone obtained was 92.4%.

Example 3: Synthesis of 2-(2-methylallyl)cyclododecanone

[Chemical Formula 21]

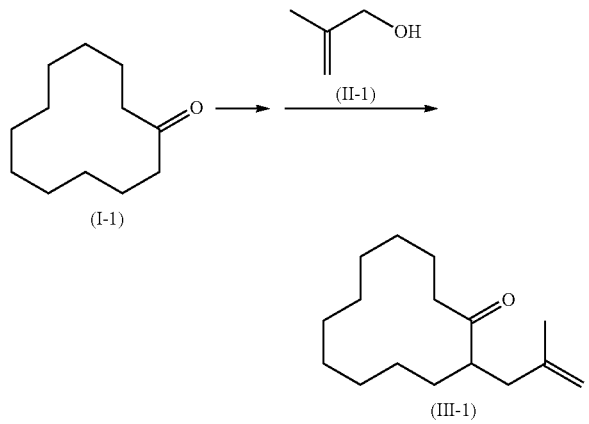

(i) Step 1

A mechanical stirrer and a Dimroth condenser were installed on a reaction container with a side arm (manufactured by EYELA, φ30). Cyclododecanone (I-1) (4.4 g, 24.1 mmol), triethyl orthoformate (8.6 g, 58.2 mmol), ethanol (6.6 g, 140.4 mmol), and pyridinium p-toluenesulfonate (0.035 g, 0.13 mmol) were placed thereinto, and were heated and refluxed at a bath temperature of 85° C. for 36 hours while being stirred.

After the reaction mixture had been cooled, B-methallyl alcohol (II-1) (5.2 g, 72.0 mmol) was added to the reaction mixture. A Dean-Stark trap was installed, the bath temperature was raised to 140° C., and then the reaction mixture was heated and refluxed for 11 hours.

After the reaction solution had been cooled, a saturated aqueous solution of sodium hydrogen carbonate (10 mL) was added to the reaction solution, and the resultant mixture was stirred for 5 minutes. The oil layer of the obtained reaction end product was diluted with diethyl ether, and then the aqueous layer was removed. The solvent in the oil layer was distilled off under reduced pressure, and thus a reaction end solution was obtained (7.0 g). 2-(2-Methylallyl)cyclododecanone (III-1) in the reaction end solution corresponded to 79.2 GC area %, and the yield was 92.4%.

[Chemical Formula 22]

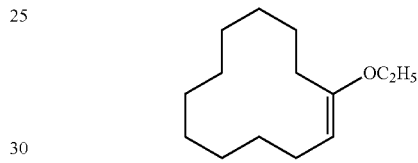

(XXI-2)

(ii) Step (ii)

A K-shaped pipe, a cooling pipe, and a distillate receiver were installed on a 300-mL four-neck flask containing the reactants. Under a nitrogen atmosphere, 8-methallyl alcohol (II-1) (29.7 g, 0.411 mol) was dripped into the four-neck flask over 2 minutes while the reactants were heated and stirred at a bath temperature of 110° C. Ethanol was distilled off over 3 hours under nitrogen stream into the four-neck flask (distilled-off amount: 11.54 g). After the flow of ethanol had stopped, the K-shaped pipe, the cooling pipe, and the distillate receiver were removed from the four-neck flask, a Dimroth condenser was attached to the four-neck flask, the bath temperature was raised to 130° C., and then the reaction mixture was heated and refluxed for 4 hours. As a result of gas chromatography analysis on the obtained reaction solution, the component composition was as follows: 2-(2-methylallyl)cyclododecanone (III-1) corresponded to 93.9 area %. It should be noted that the yield of 2-(2-methylallyl)cyclododecanone (III-1) calculated from the GC area % thereof was 99.2%.

Table 1 below shows the details of all of the examples above.

TABLE 1

| Raw material | Alcohol in step 1 | First acid catalyst in step 1 and second acid catalyst in step 2 | Equivalent of first acid catalyst and second acid catalyst relative to raw material[*1] | Compound of Formula (II) in step 2 | Yield of compound of Formula (III) (%) |
|---|---|---|---|---|---|
| Ex. 1 Compound of Formula (I-1) | Methanol | PPTS | 0.001 | Compound of Formula (II-1) | 98.1 |
| Ex. 2 Compound of Formula (I-1) | Methanol | PPTS | 0.001 | Compound of Formula (II-1) | 92.4 |

TABLE 1-continued

| Raw material | Alcohol in step 1 | First acid catalyst in step 1 and second acid catalyst in step 2 | Equivalent of first acid catalyst and second acid catalyst relative to raw material[*1] | Compound of Formula (II) in step 2 | Yield of compound of Formula (III) (%) |
|---|---|---|---|---|---|
| Ex. 3 Compound of Formula (I-1) | Ethanol | PPTS | 0.003 | Compound of Formula (II-1) | 99.2 |

[*1] "Raw material" means the compound of General Formula (I).

As can be appreciated from Table 1 above, with the method of the present invention, it is possible to obtain a highly pure compound of Formula (III) in increased yield from a compound of Formula (I).

In Examples 4 to 7, the yield of 2-(2-methylallyl)cyclododecanone (III-1) was determined in accordance with the similar procedure. The procedure for Example 4 is described below as a representative procedure, and the addition amounts of reagents are shown in the other examples.

Example 4

[Chemical Formula 23]

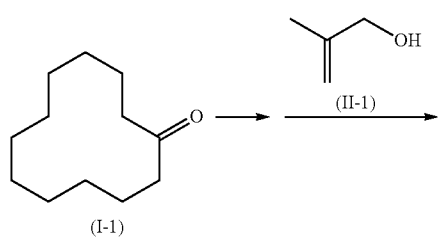

A mechanical stirrer and a Dimroth condenser were installed on a reaction container with a side arm (manufactured by EYELA, φ30). Cyclododecanone (I-1) (4.4 g, 24.1 mmol), trimethyl orthoformate (3.0 g, 28.7 mmol), methanol (2.3 g, 72.4 mmol), and p-toluenesulfonic acid (0.022 g, 0.12 mmol) were placed thereinto, and were heated and refluxed at a bath temperature of 80° C. for 3 hours while being stirred.

After the reaction mixture had been cooled, 6-methallyl alcohol (II-1) (2.6 g, 36.0 mmol) was added to the reaction mixture. A Dean-Stark trap was installed, the bath temperature was raised to 140° C., and then the reaction mixture was heated and refluxed for 2 hours.

After the reaction solution had been cooled, a saturated aqueous solution of sodium hydrogen carbonate (10 mL) was added to the reaction solution, and the resultant mixture was stirred for 5 minutes. The oil layer of the obtained reaction end product was diluted with diethyl ether, and then the aqueous layer was removed. The solvent in the oil layer was distilled off under reduced pressure, and thus a reaction end solution was obtained (5.8 g). 2-(2-Methylallyl)cyclododecanone (III-1) in the reaction end solution corresponded to 93.8 GC area %, and the yield was 95.5%.

Example 5

The procedure was the same as that for Example 4, except that the amounts of the reagents were changed as follows:

cyclododecanone (I-1) (4.4 g, 24.1 mmol), trimethyl orthoformate (3.0 g, 28.7 mmol), methanol (2.3 g, 72.4 mmol), p-toluenesulfonic acid (0.005 g, 0.027 mmol), and β-methallyl alcohol (II-1) (2.6 g, 36.0 mmol). The weight of the reaction end solution was 5.4 g. 2-(2-Methylallyl)cyclododecanone (III-1) corresponded to 95.8 GC area %, and the yield was 90.9%.

Example 6

The procedure was the same as that for Example 4, except that the amounts of the reagents were changed as follows:

cyclododecanone (I-1) (4.4 g, 24.1 mmol), trimethyl orthoformate (3.0 g, 28.7 mmol), methanol (2.3 g, 72.4 mmol), (+)-10-camphorsulfonic acid (0.06 g, 0.25 mmol), and β-methallyl alcohol (II-1) (2.6 g, 36.0 mmol). The weight of the reaction end solution was 5.9 g. 2-(2-Methylallyl)cyclododecanone (III-1) corresponded to 95.3 GC area %, and the yield was 90.9%.

Example 7

The procedure was the same as that for Example 4, except that the amounts of the reagents were changed as follows:

cyclododecanone (I-1) (4.4 g, 24.1 mmol), trimethyl orthoformate (3.0 g, 28.7 mmol), methanol (2.3 g, 72.4 mmol), pyridine hydrochloride (0.26 g, 2.5 mmol), and B-methallyl alcohol (II-1) (2.6 g, 36.0 mmol). The weight of the reaction end solution was 5.4 g. 2-(2-Methylallyl)cyclododecanone (III-1) corresponded to 77.1 GC area %, and the yield was 73.7%.

Tables 2 and 3 below show the details of all of Examples 4 to 7 above and the results obtained therefrom.

TABLE 2

| Raw material | Alcohol in step 1 | First acid catalyst in step 1 and second acid catalyst in step 2 | Equivalent of acid catalysts relative to raw material[*1] | Compound of Formula (II) in step 2 | Yield of compound of Formula (III) (%) |
|---|---|---|---|---|---|
| Ex. 4 Compound of Formula (I-1) | Methanol | PTS | 0.005 | Compound of Formula (II-1) | 95.5 |
| Ex. 5 Compound of Formula (I-1) | Methanol | PTS | 0.001 | Compound of Formula (II-1) | 90.9 |

[*1]"Raw material" means the compound of General Formula (I).

TABLE 3

| Raw material | Alcohol in step 1 | First acid catalyst in step 1 and second acid catalyst in step 2 | Equivalent of acid catalysts relative to raw material[*1] | Compound of Formula (II) in step 2 | Yield of compound of Formula (III) (%) |
|---|---|---|---|---|---|
| Ex. 6 Compound of Formula (I-1) | Methanol | (+)-10-camphorsulfonic acid | 0.01 | Compound of Formula (II-1) | 90.9 |
| Ex. 7 Compound of Formula (I-1) | Methanol | Pyridine hydrochloride | 0.1 | Compound of Formula (II-1) | 73.7 |

[*1]"Raw material" means the compound of General Formula (I).

As can be appreciated from Tables 2 and 3 above, with the method of the present invention, it is possible to obtain a highly pure compound of Formula (III) in increased yield from a compound of Formula (I).

INDUSTRIAL APPLICABILITY

With the production method of the present invention, it is possible to produce a highly pure compound of Formula (III) in increased yield. Furthermore, the production method of the present invention is useful for a method for producing muscenone.

The invention claimed is:

1. A method for producing an α-allylated cycloalkanone represented by Formula (III-1), comprising:
   1: reacting a compound represented by Formula (I-1) and an alcohol having 1 or more and 4 or less of carbon atoms in the presence of a first acid catalyst and optionally a dehydrating agent; and
   2: reacting a crude product obtained in the reacting 1 and a compound represented by Formula (II) in the presence of a second acid catalyst to produce an α-allylated cycloalkanone represented by Formula (III-1),
   wherein the reacting 1 and the reacting 2 are consecutively performed without isolating a compound of Formula (XX) or a compound of Formula (XXI) after said reacting 1

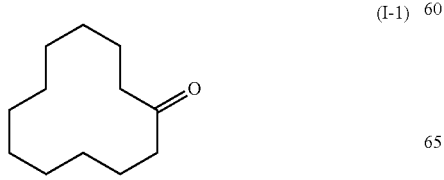
(I-1)

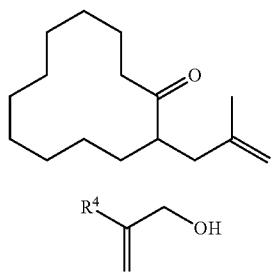
(III-1)

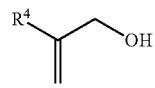
(II)

wherein $R^4$ is alkyl group having 1 carbon atom,

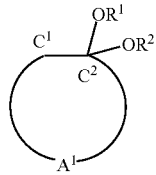
(XX)

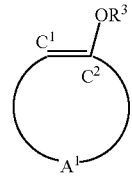
(XXI)

wherein:
   $R^1$, $R^2$ and $R^3$ are the same or different and each of them is an alkyl group having 1 or more and 4 or less of carbon atoms, and
   the group -$A^1$- is an alkylene group having 10 carbon atoms, where the front bond of the group -$A^1$- refers to a bond that binds to the carbon atom $C^1$ and the back bond of the group $-A^1-$ refers to a bond that binds to the carbon atom $C^2$.

2. The method according to claim 1, further comprising removing the alcohol having 1 or more and 4 or less of carbon atoms in the presence of the first acid catalyst after reacting 1.

3. The method according to claim 1, wherein the method in which the reacting 1 and the reacting 2 are consecutively performed comprises no isolation-purification step performed in the course of the method.

4. The method according to claim 1, wherein the first acid catalyst and the second acid catalyst are independently one or more selected from the group consisting of organic sulfonic acids and salts thereof, and inorganic acid salts of pyridine.

5. The method according to claim 4, wherein the organic sulfonic acids are aromatic sulfnic acids.

6. The method according to claim 4, wherein the first acid catalyst and the second acid catalyst are independently selected from the group consisting of compounds represented by Formula (X) below and compounds represented by Formula (XI) below:

(X)

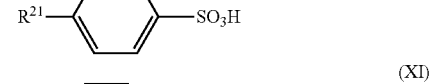
(XI)

(XII)

(XIII)

where $R^{21}$ and $R^{22}$ are independently a hydrogen atom or an alkyl group having 1 or more and 5 or less of carbon atoms, and $X^4$ is represented by Formula (XII) or Formula (XIII), and where $R^{11}$, $R^{12}$, $R^{13}$, and $R^{14}$ are the same or different and each of them is a hydrogen atom or an alkyl group having 1 or more and 5 or less of carbon atoms.

7. The method according to claim 1, wherein the first acid catalyst and the second acid catalyst independently comprises p-toluenesulfonic acid or pyridinium p-toluenesulfonate.

8. The method according to claim 4, wherein the salts of the organic sulfonic acids are pyridinium salts.

9. The method according to claim 4, wherein an acid included in the inorganic acid salts of pyridine is one or more selected from the group consisting of hydrochloric acid, sulfuric acid, nitric acid, phosphoric acid, sulfurous acid, nitrous acid, hydrobromic acid, hydroiodic acid, acetic acid, and butyric acid.

10. The method according to claim 1, wherein the first acid catalyst and the second acid catalyst are the same.

11. The method according to claim 1, wherein an amount of the first acid catalyst that is used is 10-5 equivalents or more and 1 equivalent or less relative to a total amount of the compound of General Formula (I) and the compound of General Formula (II).

12. The method according to claim 1, wherein the reacting 1 and the reacting 2 are performed using a rectification column.

13. The method according to claim 1, wherein the reacting 1 and the reacting 2 are performed in one pot.

14. A method for synthesizing muscenone, the method comprising:
1: reacting a compound represented by Formula (I-1) and an alcohol having 1 or more and 4 or less of carbon atoms in the presence of a first acid catalyst and optionally a dehydrating agent;
2: reacting a crude product obtained in the reacting 1 and β-methallyl alcohol in the presence of a second acid catalyst to produce an α-allylated cycloalkanone represented by Formula (III-1),
(i) cyclization of the α-allylated cycloalkanone represented by Formula (III-1);
(ii) hydrogenation;
(iii) oxidative cleavage;
(iv) reduction; and
(v) ring-opening,

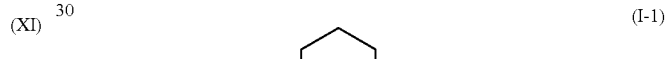
(I-1)

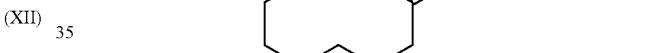
(III-1)

wherein the reacting 1 and the reacting 2 are consecutively performed without isolating a compound of Formula (XX) or a compound of Formula (XXI) after said reacting 1

(XX)

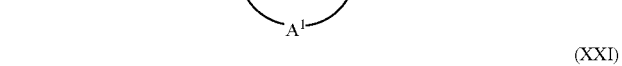
(XXI)

wherein

R$^1$, R$^2$ and R$^3$ are the same or different and each of them is an alkyl group having 1 or more and 4 or less of carbon atoms, and the group -A$^1$- is an alkylene group having 10 carbon atoms, where the front bond of the group -A$^1$- refers to a bond that binds to the carbon atom C$^1$ and the back bond of the group -A$^1$- refers to a bond that binds to the carbon atom C$^2$.

15. The method according to claim 14, further comprising removing the alcohol having 1 or more and 4 or less of carbon atoms in the presence of the first acid catalyst after reacting 1.

\* \* \* \* \*